Figure 1:
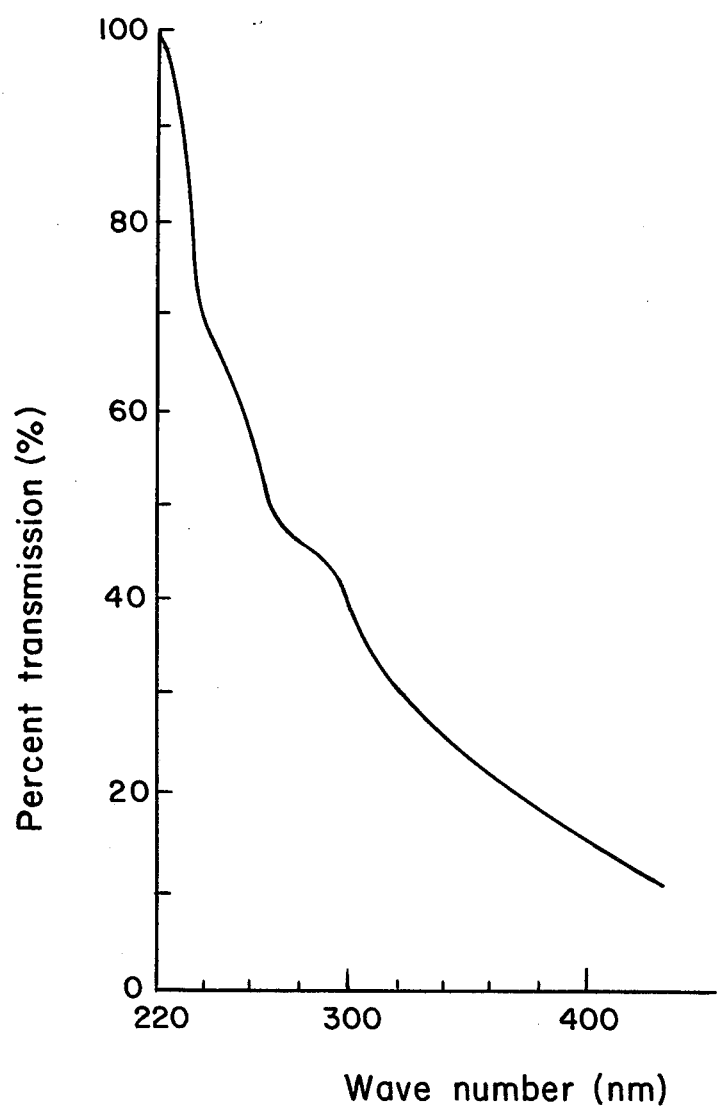

United States Patent [19]

Kojima et al.

[11] 4,456,597

[45] * Jun. 26, 1984

[54] INTERFERON INDUCER, A PROCESS FOR PRODUCING THE SAME AND PHARMACEUTICAL COMPOSITION CONTAINING THE SAME

[75] Inventors: Yasuhiko Kojima, Yokohama; Seishi Konno, Tokyo; Takashi Hashimoto, Chofu, all of Japan

[73] Assignee: The Kitasato Institute, Tokyo, Japan

[*] Notice: The portion of the term of this patent subsequent to Apr. 3, 2001 has been disclaimed.

[21] Appl. No.: 290,284

[22] Filed: Aug. 6, 1981

Related U.S. Application Data

[63] Continuation-in-part of Ser. No. 119,325, Feb. 7, 1980, abandoned.

[30] Foreign Application Priority Data

Aug. 6, 1980 [JP] Japan .................................. 55-107954

[51] Int. Cl.$^3$ .............................................. A61K 31/69
[52] U.S. Cl. .................................................... 424/195
[58] Field of Search ......................................... 424/195

Primary Examiner—Stanley J. Friedman
Attorney, Agent, or Firm—Wolder, Gross & Yavner

[57] ABSTRACT

An interferon inducer isolated from the plant tissue, having an elemental analysis of H: 6.54±0.3% C: 41.9±0.3%, N: 2.39±0.3% and P: 0.28±0.03% and a molecular weight of from about 100,000 to about 3,000,000 (mainly about 200,000 to about 1,000,000) and containing as main constituents amino acids, sugars and phosphoric acid. This substance is believed to be a homogeneous polymer of protein and sugars, containing phosphoric acid. This substance has an excellent interferon inducing activity and low toxicity and is significantly active against various viruses. The interferon inducer may be produced by extracting a substance having interferon inducing activity from the tissue of a plant of the genus Carthamus of the family Compositae or a variant thereof containing said active substance and recovering the active substance from the extract thereby obtained. Preferably, the active substance may be extracted from the flower of this plant with water and the recovery may be effected by ultrafiltration using a membrane capable of fractionating substances having a molecular weight of from 200,000 to 1,000,000. Pharmaceutical composition of this invention comprises as active ingredient the interferon inducer of this invention in association with a pharmaceutical carrier or excipient.

14 Claims, 2 Drawing Figures

INTERFERON INDUCER, A PROCESS FOR PRODUCING THE SAME AND PHARMACEUTICAL COMPOSITION CONTAINING THE SAME

RELATED APPLICATION

This application is a continuation-in-part of Ser. No. 119,325 filed Feb. 7, 1980, now abandoned.

BACKGROUND OF THE INVENTION

This invention relates to interferon inducer, a process for producing the same, the use of the same and a pharmaceutical composition containing the same.

Interferon, hereinafter also referred to as IF, is a substance capable of acting upon animal or human cells to inhibit the growth of a virus and is a type of protein liberated from the cell in response to viral infection. The activity of IF is specific with respect to an animal species and non-specific with respect to a viral species and may vary, with differing conditions used for its induction. It is also known that the growth of certain animal tumour type viruses may significantly be inhibited by IF under certain conditions.

A substance capable of acting upon animal or humans cells to induce IF is designated as an IF inducer. Thus an IF inducer is of potential interest in the prevention and treatment of various human and animal diseases caused by viral infection. However, various known IF inducers have never been used in practice for such a purpose because of certain serious defects. Thus, for example, U.S. Pat. No. 3,583,893 (1971) discloses the production of a double-stranded ribonucleic acid as an IF inducer originating from a microorganism and describes in its prior art statement that many substances including bacteria, viruses, polysaccharides, mitogenic agents, endotoxin and the like stimulate interferon formation but none is of interest for routine use because of their inter alia toxicity, antigenicity and infectiousness. It has thus been believed that IF inducers isolated from microorganisms are in general disadvantageous for therapeutic use because of their high toxicity.

Examples of known mitogenic agent isolated from the tissues of higher plants include phytohemagglutinin (PHA) [Wheelock, Science, 149:301 (1965) and J. Biol. Chem., 212: 607–615 (1955)], pokeweed mitogen[Friedman et al, Proc. Soc. Exp. Med., 125:90 (1967) and J. Exp. Med., 124:859–872 (1966)] and concanavallin A [Willen et al, Cell. Immunol., 6:110 (1973) and Methods of Carbohydrate Chemistry, Vol. VI. 108–110 (1972)] respectively isolated from the tissues of kidney bean, pokeweed and horse bean by extracting with a saline solution or buffer solution, treating the extracted solution with an alcohol, followed by purification with column chromatography. Due to their extremely low IF-inducing activity, however, no successful attempt has been made to use these mitogenic agents for preventing and treating various diseases caused by viral infection.

Other IF inducers isolated from higher plants are also known. That is, Kojima et al [Japanese Patent Application as laid open to public inspection as Kokai Koho 32107/78] disclosed an IF inducer which is believed to be a kind of heteropolymeric saccharide containing as main constituents hexose (48%), protein (5%) and uronic acid (40%) and having a molecular weight of more than 100,000. This substance is isolated from the root of *Angelica acutiloba* Kitagawa (known in Japan as Toki) by extracting the root with hot water to give an extracted solution, subjecting the same to dialysis to give a residue, adding acetone to the residue to give a precipitate and freeze-drying the same. The extracted solution may, if desired, be made up to a suitable quantity by concentrating under reduced pressure or by using a Diaflo membrane (MW 10,000), followed by dialysis. Subsequently, Kojima and Tamamura [Japanese Patent Application laid open to public inspection as Kokai Koho 99313/78] disclosed an IF inducer having a molecular weight of more than 20,000 (mainly more than 60,000) and containing as main constituents a 1-3 bonded glucose (hexose: more than 90%). This IF inducer is produced by extracting the peeling of a mulberry e.g. *Morus alba* L. or *M. bombycis* Koidzumi with hot water, adding an organic solvent to the extracted solution to give a precipitate, adding a small amount of water to the same, subjecting the mixture to dialysis to give a residue and freeze-drying the same. If desired, the solution after extraction or before dialysis may be made up to a suitable quantity either by concentrating under reduced pressure or by using a Diaflo membrane.

These two IF inducers isolated from the tissues of higher plants have high IF-inducing activity and low toxicity and may be obtained readily and cheaply. However, the cheap and abundant supply of the raw material may cease as a result of the continued use of these plants over many years as the source of Sino-Japanese traditional drugs.

SUMMARY OF THE INVENTION

The present invention is based upon the discovery that a substance which we have isolated from the tissue of various plants of the genus Carthamus of the family Compositae (known in Japan as the genus Benibana of the family Kiku) and variants thereof shows high IF-inducing activity and extremely low toxicity. Moreover, the isolation of the active substance may be effected readily and simply.

According to this invention, there is provided a substance having IF-inducing activity which is stable in the substantially pure form of an amorphous whitish powder and which possesses the following physico-chemical characteristics:

(1) Elemental analysis:
H: $6.54\pm0.3\%$, C: $41.9\pm0.3\%$, N: $2.39\pm0.3\%$, P: $0.28\pm0.03\%$ (2) Molecular weight: About 100,000 to about 3,000,000 (mainly about 200,000–about 1,000,000).

(3) Melting or decomposing point: Melting point indefinite. Carbonized at about 220° C.

(4) Ultraviolet absorption spectrum: As shown in FIG. 1 (in 0.1N NaOH solution) which is unchanged in water or 1N NaOH solution.

Figure 2:
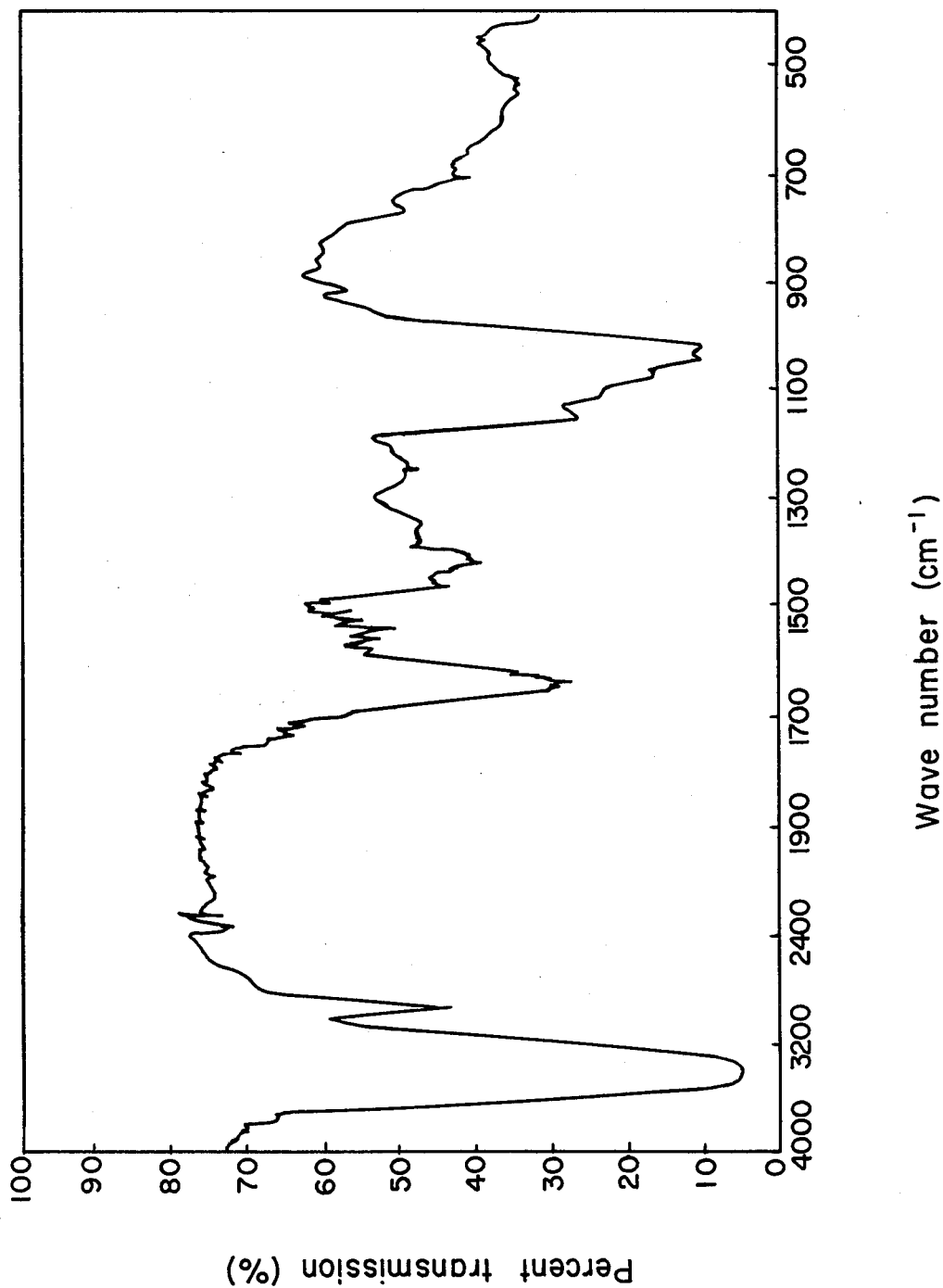

(5) Infrared absorption spectrum: As shown in FIG. 2 (by KBr method)

(6) Solubility in various solvents: Soluble in water, readily soluble in aqueous solutions of sodium hydroxide, potassium hydroxide and ammonium hydroxide, and substantially insoluble in methanol, ethanol, propanol, butanol, acetone, chloroform and diethyl ether.

(7) Color reaction: Positive in ninhydrin reaction, phenol/sulfuric acid reaction, Folin's reagent and Dittmer reaction, and negative in Elson-Morgan reaction.

(8) Nature: Acidic.

(9) Main chemical constituents:

| (a) Amino acids ±0.4 (%): | | | |
|---|---|---|---|
| Oxyproline | 15.61 | aspartic acid | 5.51 |
| threonine | 10.90 | serine | 9.64 |
| glutamic acid | 3.96 | proline | 4.27 |
| glycine | 9.09 | alanine | 8.24 |
| valine | 4.04 | isoleucine | 5.59 |
| leucine | 2.56 | phenylalanine | 1.32 |
| lysine | 2.18 | arginine | 1.24 |
| thyrosine | 1.94 | histidine | 0.93 |
| ammonia | 12.98 | | |
| (b) Sugars ±0.6 (%): | | | |
| Arabinose | 9.38 | galactose | 20.98 |
| glucose | 64.98 | mannose | 3.26 |
| xylose | 1.40 | | |

(10) Optical rotation: $[\alpha]_D^{26} = +63°$ to $+69°$ ($+66°$ in average) (c=0.49% in 0.1N NaOH)

The elemental analysis of the active substance of this invention was determined by using a Perkin-Elmer Model 240 Elemental Analyzer (commercial product of Perkin-Elmer Corpn., U.S.A.). The molecular weight of the active substance of this invention was determined by analytical ultracentrifugation using a Spinco Model E Analytical Centrifuge (commercial product of Beckmann Instrument Inc., U.S.A.), ultrafiltration using an Amicon Ultrafilter with XM50, XM100A and XM300 membranes (commercial products of Amicon Corpn., U.S.A.) and UK10, UK50 and UK200 membranes (commercial products of Toyo Roshi K.K., Tokyo) and gel filtration using Sephadex G-200 (commercial product of Pharmacia Fine Chemicals AB., Sweden). The ultracentrifugation was effected under the following conditions and one broad peak having gentle slopes on both sides was observed: A sample (0.5-1.0%) of the active substance was suspended in a neutral solution of 0.1M sodium chloride and centrifuged at 20° C. at a maximum run of 30,000 or 60,000 r.p.m. Supplementarily, column chromatography using gel filtration agents such as e.g. the series of Sepharose, Sephacryl (commercial products of Pharmacia Fine Chemicals AB., Sweden) and Bio-Gel (commercial products of Bio-Rad Laboratories Ltd., U.S.A.) were also used. All the results obtained were compared with the control values obtained, for example, by using standard references having identified molecular weights such as e.g. blue dextran 2000 (*2×10[6]), $\alpha_2$-macroglobulin from horse serum (*8×10[5]), thyroglobulin from bovine thyroid (*6.69×10[5]), catalase from bovine lever (*2.1×10[5]), aldolase from rabbit muscle (*1.58×10[5]) and albumin from bovine serum (*6.7×10[4]) [*.. standard molecular weight). Throughout various fractions having different molecular weights, substantially the same elemental analysis and IF-inducing activity (determined by the method of hereinafter described Experiment (1) were found. From these results, in combination with a broad single band observed by the electrophoresis (cf. hereinafter described Experiment (2) and a high recovery ratio (cf. hereinafter described Experiment (4), it is found that the active substance of this invention is not a mixture but a high molecular weight polymer composed of polymers having substantially the same chemical and biological characteristics, of which major portion is present in a range of from about 200,000 to about 1,000,000 and the minor portion is present in a range of from about 100,000–about 200,000 and about 1.000.000–about 3,000,000.

The UV and IR absorption spectra were determined respectively by using Hitachi 340 Recording Spectrophotometer (commercial product of Hitachi Limited,. Japan) and Shimazu Recording Infrared Spectrophotometer IR-27G (commercial product of Shimazu Seisaku-sho, Japan).

The amino acids present were determined by hydrolysis with 6N HCl at 110° C. for 48 hours in vacuo, followed by analysis using a Technicon Amino Acid Autoanalyzer Type NC-1 (commercial product of Technicon Corpn., U.S.A.) and the sugars present were determined by hydrolysis with 0.1N sulfuric acid at 80° C. for 20 minutes and with 1N sulfuric acid at 100° C. for 2 hours respectively, followed by analysis using a Technicon Sugar Autoanalyzer Type N-1 (commercial product of Technicon Corpn., U.S.A.).

The active substance of this invention also preferably and readily soluble in alkaline solutions and substantially insoluble in organic solvents.

The following tests were effected to ascertain that the active substance of this invention represents an IF inducer.

(1) IF-inducing activity:

Samples of the active substance of this invention were used to induce IF in the cells and serum of test animals and the activity of the resultant IF was determined by the methods hereinafter described in Experiment 1. The results shown in Table 1 indicates that the IF inducing activity is positive.

TABLE 1

| | Concentration of sample (μg/ml) | | | |
|---|---|---|---|---|
| | 10 | 1.0 | 0.1 | 0.01 |
| Activity in vitro | >100 | >100 | 96 | <10 |

TABLE 2

| Activity in vivo* | Time of collection of blood after administration (hour) | | | | |
|---|---|---|---|---|---|
| | 0 | 1 | 2 | 4 | 5 |
| Rabbit 1 | 15 | 80 | 470 | 175 | 50 |
| Rabbit 2 | 15 | 80 | 500 | 280 | 70 |

*Dose = μg/ml

Table 2 indicates that the results obtained by the method hereinafter described in Experiment 1 using two rabbits show the activity reaches its maximum 2 hours after administration. It was also confirmed that by the method of Experiment 1, IF was induced in the body of the test animals by the action of the IF inducer of this invention.

(2) Stability of the IF inducer:

Samples (each 1 mg) of the IF inducer of this invention were respectively dissolved in water (each 1 ml) and heated at 100° for a given time or at a given temperature for one hour, and was then treated by the method of hereinafter described in Experiment 1 (in vitro method) to obtain the results shown in Tables 3 and 4 indicating a high heat stability of the IF inducer of this invention.

TABLE 3

| Heating temperature (C.°) | Activity at Concentration of sample (μg/ml) | | | |
|---|---|---|---|---|
| | 10 | 1.0 | 0.1 | 0.01 |
| | IF activity | | | |
| Untreated | >100 | >100 | 90 | <10 |
| 37 | >100 | >100 | 95 | <10 |

TABLE 3-continued

| Heating temperature (C.°) | Activity at Concentration of sample (μg/ml) | | | |
|---|---|---|---|---|
| | 10 | 1.0 | 0.1 | 0.01 |
| 60 | >100 | >100 | 90 | <10 |
| 80 | >100 | >100 | 92 | <10 |
| 100 | >100 | >100 | 93 | <10 |

Heating time: one hour.

TABLE 4

| Heating time (hour) | Activity at Concentration of sample (μg/ml) | | | |
|---|---|---|---|---|
| | 10 | 1.0 | 0.1 | 0.01 |
| Untreated | >100 | >100 | 92 | <10 |
| 1 | >100 | >100 | 95 | <10 |
| 4 | >100 | >100 | 93 | <10 |
| 8 | >100 | >100 | 65 | <10 |
| 24 | >100 | >100 | 35 | <10 |

Heating temperature: 100° C.

From the above-mentioned characteristics, it has been found that the active substance of this invention conforms to widely recognized definition of any IF-inducer. The induced IF in animal cell or serum in vitro or in vivo is inactivated with 0.08% trypsin at 37° C. for 2 hours and moreover its activity is specific with respect to an animal species and non-specific with respect to a viral species.

In tables 1-4, the samples used were prepared by the method of Example 1.

It is thus believed that the active substance of this invention is not only a new IF inducer but also a new substance because no such a substance has, to our knowledge, ever been reported in the art. For example, mitogenic agents such as phytohemagglutinin, pokeweed mitogen and cncanavallin A described in the literatures are types of protein having very weak IF-inducing activity which is inactivated on heating at 56° C. for 5 hours, on the contrary to high heat stability and high IF-inducing activity of the active substance of this invention. The known IF inducers isolated from the root of *Angelica actiloba* Kitagawa is high molecular and its IF-inducing activity is not inactivated on heating at 100° C. for one hour. However, its chemical constituents and infrared absorption spectrum are different from those of the active substance of this invention. The known IF inducer isolated from the peeling of mulberry root contains as main constituent a 1-3 bonded glucose and has a different molecular weight. Moreover, the mitogenic activity which is found in the known IF inducers originating from bactrial endotoxin and higher plants such as *Angellica acutiloba* Kitagawa and mulberry is very low or not found in the IF inducer of this invention.

Various plants belonging to the genus Carthamus which may be used for the purpose of this invention are widely grown in wild or cultured in various countries of the world and are liable to form various variants such as mutants and hybrids naturally or artificially. For example, *Carthamus tinctorius* Linne (safflower) and variants thereof have been cultured and used over many years for their yellow and red pigments contained in the flower and nowadays are cultured mainly for their oil in the achens in various countries. In addition, the flower has long been used as Sino-Japanese traditional medicine in Japan and China over thousands of years. However, to our knowledge, the presence of a substance having IF inducing activity in the tissue of the plant has never been reported in the art [cf. for example, "Chinese Herbal Medicine, Ancient and Modern Science" by Richard Hyatt, page 123 (1978); "Chinese Herbs, Their Botany, Chemistry and Pharmacodynamics" by John D. Keys, pages 223-224 (1978); "Kanpo, Geschichte, Theorie und Praxis der Sino-Japanischen traditionellen Medizin" by Keisetus Otsuka, page 175 (1976)].

Various plants of the genus Carthamus which may be used as a source of the product of the IF inducer of this invention contain, for example, carthamine, carthamone, neocarthamine and the like, all of which are low molecular weight substances having no IF inducing activity. The physico-chemical characteristics of the known IF inducers disclosed, for example, in U.S. Pat. No. 3,583,893; 3,773,924 and 3,884,845 and Japanese Patent Kokai Koho 121919/78 are different from those of the IF inducer of this invention.

According to another feature of this invention, we provide a process for producing an interferon inducer from the plant tissue, comprising extracting the said IF inducer with water from the tissue of a plant selected from the genus Carthamus and variants thereof containing the said IF inducer at a temperature from ambient to the boiling point of the extraction mixture for a period sufficient to extract the major portion of the IF inducer present in the tissue, forming a supernatant from the extracted solution, fractionating the supernatant to yield fractions containing a major portion of the IF inducer present in the supernatant, and recovering the IF inducer therefrom.

The plants of the genus Carthamus which may be used as a source of the product of this invention are annual herbs grown in wild or cultured in various countries of the world. Ant and all parts of the genus Carthamus may be used for the purpose of this invention when they contain the active substance of this invention, and the following plants are merely indicated by way of example:

*Carthamus tinctorius* Linne; *C. lanatus* L.;
*C. arborescens* L; and variants thereof such as *C. baeticus* Nyman.

The botanical names referred to in this specification are designated with reference to "Yakuyo Shokubutsu Dai Jiten", edited by Kariyone and Kimura and published by Hirokawa Shoten, Tokyo (1974); "Saishin Yakuyo Shokubutsu" by Kariyone and Kimura and published by Hirokawa Shoten, Tokyo (1978); "Flora Europaea", vol. 4, published by Cambridge University Press, London (1976); and "Illustrated Flora of The Pacific States", vol. IV by Stanford University Press, CA. (1965).

The extraction may be effected with water at any convenient temperature, e.g., from ambient to the boiling point of the extraction mixture. Because the active substance of this invention is particularly soluble in water under alkaline conditions (e.g. at a pH of 7-10), it is preferred to adjust the pH of water before use, for example, with a suitable buffer solution, sodium hydroxide, potassium hydroxide, ammonium hydroxide and the like. The extraction may be effected over any convenient period of time, usually 1-5 days at room temperature, which may be shortened if the extraction temperature is raised. Thus, for example, the extraction may be effected for a period of time from 30 minutes to 6 hours at 45°-80° C. with or without stirring. In this manner, it is possible to extract a major portion of the active substance contained in the starting material (in some cases, more than 90%). However, the use of an excessively high temperature should be avoided because the quantity of undesired impurities such as e.g. pigments, low molecular weight substances and the like appearing in the extract may thereby increase. It is also possible to add a suitable antiseptic agent to the extracting water. The extraction may be effected continuously or intermittently at any convenient ratio of the extracting water to the raw plant.

It is also possible, if desired to extract the active substance with a hydrophilic organic solvent incapable of dissolving the IF inducer of this invention such as e.g. methanol, ethanol, propanol, butanol, acetone and the like in any convenient amount e.g. 20–80%. In such a case, the extraction time and temperature may be convenient e.g. for 4 hours to 2 days at 40° to 80° C. In such cases, the extraction may be effected by using a hydrophilic organic solvent in spite of the insolubility of the pure product of this invention in such solvents, for example when the extracted solution contains a mixture of complex of substances such as e.g. fatty acids, steroids, proteins, mono- or polysaccharides and the like. Whilst we do not wish to be bound with theoretical considerations, it is believed that extraction using such solvents is made possible by buffer action. However, extraction with water is most advantageous because it is simpler, cheaper and safer in operation.

The residue of the plant tissue is then removed from the extracted solution in conventional manner, for example, by filtration, pressing, centrifugation and the like. After this, undesired impurities such as pigments and low molecular weight substances are removed from the resultant supernatant in order to allow recovery of the active fraction. Preferred methods for this purpose are exemplified as follows.

(A) The supernatant is fractionated by ultrafiltration e.g. using a suitable membrane for fractionating substances having a molecular weight of more than 100,000 because the active substance of this invention is present in fractions having a molecular weight of about 100,000 to about 3,000,000 (mainly about 200,000 to 1,000,000). The ultrafiltration may be effected under suitable pressure, for example, 0.1 to 5 kg/cm$^2$ by using a membrane capable of retaining substances having a molecular weight of more than 100,000 or 200,000. The active fractions are collected and combined and the combined fractions are freeze-dried to obtain brown powders.

(B) The supernatant is concentrated, is desired, under reduced pressure and is treated with a hydrophilic organic solvent (e.g. methanol, ethanol, propanol, n-butanol, acetone and the like) at a convenient concentration (e.g. 40–70 w/v %) so as to form precipitates containing the active substance. The precipitates are freeze-dried to obtain brown powders.

(C) Instead of the organic solvent, it is possible to add to the supernatant an ammonium salt (e.g. ammonium chloride, ammonium sulfate, cetylmethylammoniumbromide and the like) or an inorganic metalic salt (e.g. zinc chloride, copper chloride and the like) at a convenient concentration (e.g. 20 to 50 w/v %) so as to form precipitates which are then desalted and freeze-dried to obtain brown powders.

It is possible to recover the major portion of the active substance contained in the starting material (in some cases, more than 90%). However, the quantity of impurities contained in the crude powder is lowest in the case of method (A), and also method (A) may be effected simply. Moreover, it has been confirmed that any significant side effect may be avoided even when a large amount of the crude powder obtained by (A) is orally administered to humans and animals and thus this crude powder may be used for oral administration without further purification.

If desired, the crude powder thus obtained may further be purified, for example, by column chromatography using a suitable agent for gel filtration or an ion exchanger. In the former case, the elution may be effected with water, although it is possible to use a suitable buffer solution. In the latter case, the elution may be effected with a suitable buffer solution. Preferable agents for gel filtration are exemplified by Sephadex G-50 to G-200, Sepharose 2B to 6B, Sephacryl S-200 or S-300 (commercial products of Pharmacia Fine Chemicals AB., Sweden), Bio-Gel P-30 to P-300, Bio-Gel A (commercial products of Bio-Rad Laboratories Ltd., U.S.A.), Sagavac (commercial product of Saravac Laboratories Ltd., U.K.) and the like, and preferred agents for ion exchange treatment are exemplified by QAE-Sephadex A-25 and A-50 (Cl$^-$ form), CM-Sephadex C-25 and C-50 (Na$^+$ form), DEAE-Sephacel (Cl$^-$ form), DEAE-Sepharose CL-6B (Cl$^-$ form), CM-Sepharose CL-6B (Na$^+$ form) (commercial products of Pharmacia Fine Chemicals AB., Sweden) and the like. It is also possible to use a suitable anion or cation exchange cellulose for the purification. The product thus-obtained may contain certain impurities, although its IF inducing activity is sufficient for practical purposes. If desired, the amount of impurities may be further reduced by combining these treatments.

According to a further feature of this invention, there is provided a process for inducing an IF in the body or cells of human or animal, which comprises administering an effective amount of the IF inducer of this invention to a human or IF-inducing animal.

The active substance of this invention may be used without any toxic trouble which is inherent to various known IF inducers such as e.g. polyI:C, endotoxin and the like. Moreover it has also been found that when administered to humans, the activity of the IF inducer of this invention is superior to those of the known IF inducers. The IF inducer of this invention is capable of not only affording a high antiviral activity but also enhancing anti-tumour activity and overall physiological activities. It is thus possible to use the IF inducer of this invention not only for the prevention and curing of various virally caused diseases of various vetebrates such as, for example, humans, mammals (e.g. cattle, horse, pig etc.), birds (e.g. fowl, duck etc.), fishes (e.g. rainbow trout etc.) and the like but also as anti-tumour agent, agent for improving overall healthy conditions for humans and animals.

The active substance of this invention may be administered e.g. by intravenous or intraperitoneal administration, intestinal or oral administration, spraying and the like.

In the case of intravenous administration, it may be possible to administer the active substance at a dose of 0.001 to 100 mg/kg/day, calculated as the final product. However, such a dose may vary, depending upon, for example, the type, age and weight of the host and various other conditions, among which the response of the host to IF induction and the purpose of the administration are most important. The active substance of this invention may preferably be administered to animals, for example, at a daily dose of 0.01 to 10 mg/kg (iv.) or 0.1 to 10 mg/kg (ip.) and to humans at a daily dose of 0.01 to 1.0 mg/kg (iv.) by injection. In the case of oral administration, it is preferred to use, for example, more than about 10 times of the dose for intravenous administration. When the administration is effected topically or in a shorter period of time, a larger amount of the active substance may be used. When the dose is excessively small, it may be difficult to induce IF in the body or cells of the host. However, the use of an excessively large amount of the active substance of this invention may, in general, give rise to no serious side effect because its toxicity is extremely low.

It has also been found that when a suitable amount of any IF is administered to a host, followed by administering the active substance of this invention, the activity of the IF induced by the active substance of this invention may significantly be enhanced and for example about 3-10 folds activity may be obtained thereby. Moreover, it is possible in this manner to enhance considerably the response of the host to IF induction and also to extend the effective period of time of the IF induced.

The following samples were used in the following tests:

Sample A ... The crude powder obtained by ultrafiltration by the method of Example 1 and freeze-dried.

Sample B ... The finally purified product by the method of Example 1.

Sample C ... The finally purified product by the method of Example 2.

As test animals, rabbits (same type as that used in hereinafter described Experiment 1), mice (weight 25±1 g, ddy-strain, 6 weeks old) and fowls (weight about 230 g, White Leghorn, 30 days old, female) were used.

(A) IF induction and determination of IF activity (I) In vitro method

A spleen cell suspension ($10^7$ cells/ml) was prepared by the method of hereinafter described Experiment 1 using an Eagle MEM medium (commercial product of Nissui Seiyaku K.K., Tokyo) containing a 10% calf serum (which was replaced by a 10% fetal cattle serum in the cases of human tests), each of which fraction (1 ml) was added with a given concetration of the sample and incubated overnight at a given temperature. The cultured liquor was centrifuged to separate a supernatant which was used for determining the IF activity induced. In the case of humans, the fresh spleen was collected from a man (adult deceased by external wounds) and used for the preparation of a leucocytes suspension on each occasion, and also blood was collected from the vein at the upper arm of a man (adult), from which the serum was separated to use for the preparation of a serum suspension on each occasion.

The IF activities were determined by using the cells shown in Table 5 in a similar manner to that hereinafter described in Experiment 1.

TABLE 5

| | IF induction in vitro | | |
|---|---|---|---|
| | I | II | III |
| Rabbit | 3 | 25 | RK-13 |
| Mouse | 30 | 37 | L |
| Human spleen | 2 | 25 | FL |
| Human leucocytes | 5 | 37 | FL |
| Fowl (White Leghorn) | 5 | 37 | Fibroblast |

I: Numbers in each group
II: Cultured for 24 hours at a temperature of (°C.)
III: Cells used for determination The results are shown in Table 6.

TABLE 6

| | | IF activity in vitro | | | | | Control* |
|---|---|---|---|---|---|---|---|
| | | Concentration (μg/ml) | | | | | 1.0 |
| | Sample | 100 | 10 | 1 | 0.1 | 0.01 | |
| Rabbit | A | 210 | 235 | 100 | <10 | <10 | 190 |
| | B | 230 | 240 | 235 | 115 | 30 | |
| | C | 250 | 235 | 225 | 105 | 28 | |
| Mouse | A | 180 | 70 | 35 | <10 | <10 | 80 |
| | B | 210 | 155 | 75 | 40 | <10 | |
| | C | 245 | 160 | 72 | 38 | <10 | |
| Human (spleen) | A | 28 | 30 | 12 | <10 | <10 | <10 |
| | B | 30 | 40 | 34 | 18 | <10 | |
| | C | 32 | 38 | 30 | 16 | <10 | |
| (leucocytes) | B | 26 | 18 | 12 | <10 | | |
| | A | 26 | 12 | <10 | | | |
| | B | 50 | 26 | 12 | <10 | | |
| | C | 45 | 22 | 11 | <10 | | |

*Poly I:C (II) In vivo method (1) Rabbit

Table 2 shows the IF activities induced in rabbits by the method hereinafter described in Experiment 1.

TABLE 2

| | Used sample: sample B* | | | | |
|---|---|---|---|---|---|
| IF activity | Time of collection of blood after administration of sample | | | | |
| (in vitro) | 0 | 1 | 2 | 4 | 6 (hour) |
| Rabbit 1 | <15 | 80 | 470 | 175 | 50 |
| Rabbit 2 | <15 | 90 | 500 | 280 | 70 |

*Dose: 500 μg/ml

Similar treatments were repeated by changing the dose of the sample stepwise within a range of 4 to 0.004 mg/kg, and it was found that the IF activity induced in the serum reached its maximum 2 hours after administration. Also, the maximum was observed about 10 to 13 hours after oral administration.

(2) Mouse

Mice (each group consisting of 10 mice) were used as test animals and treated as follows.

(a) Each 0.1 ml of a physiological solution of sodium chloride containing a given amount of sample B shown in Table 4 was injected into the vein at the tail of each mouse which was then allowed to stand for 1, 2, 3 or 5 hours, or (b) Each 0.2 ml of a physiological solution of sodium chloride containing a given amount of sample B shown in Table 7 was administered (ip) to each of the mice which was then allowed to stand for 2, 4 or 6 hours, or (c) Water (0.2 ml) containing a given amount of sample B shown in Table 7 was orally administered to each mouse which was then allowed to stand for 2.5, 5, 7.5, 10 or 13 hours, on each occasion.

On each occasion, the test animal was then sacrificed by cardic puncture. Blood was collected from each mouse and used to prepare the serum. The IF activity induced was determined in a similar manner to that described above. It was observed that the IF activity reached its maximum about 2 hours in the case (a), about 3-4 hours in the case (b) and about 7.5-10 hours in the case (c), after administration. Table 7 indicates the maximum IF activities (mean value). A similar tendency was also found when the same treatments were repeated by using sample A instead of sample B.

TABLE 7

| Maximum IF activity in vivo (mouse) | | | |
|---|---|---|---|
| Concentration (mg/kg) | Intravenous | Ip. | Oral |
| 4000 | | | 22 |
| 400 | | | 16 |
| 40 | 670 | 170 | <10 |
| 4 | 185 | 20 | <10 |
| 0.4 | 60 | <10 | |
| 0.04 | 18 | <10 | |
| 0.004 | <10 | <10 | |
| Untreated | <10 | <10 | <10 |

(3) Humans

Each 200 mg of sample B was orally administered to each of five men (adults, healthy). Blood was collected from the vein at the arm of each volunteer after 13 hours from administration and used for the preparation of the serum which was then treated in a similar manner to that described above to determine the IF activity of about 14 units (mean value).

(4) Fowl

Fowls (each group consisting of 10 chickens) were used as test animals. A physiological solution of sodium chloride (each 0.2 ml) containing sample B (4 mg/kg) was administered into the vein under the wing of each animal. After 2 hours on each occasion, the fowl was sacrificed by cardic puncture. Similarly, blood was collected for use to determine that the IF activity induced in the serum was about 26 units.

(B) Protection against viral infections

(1) Mouse (Vaccinia virus)

Mice (each group consisting of 20 female) were used as test animals, to each of which was administered a physiological solution of sodium chloride (each 0.2 ml) containing a given amount of the sampel shown in Table 5 intravenously, intraperitoneally or orally. After 24 hours, each mouse was infected with Vaccinia virus at a dose of of 30 $PFD_{50}$ [1 $PFD_{50}$ denotes an amount of the virus capable of forming the pocks at the tails of 50% of the mice used] contained in 0.1 ml of a physiological sodium chloride solution by injecting into the vein at the tail. For 9 days after this, the numbers of the pocks formed at the tail were compared with the corresponding numbers of the pocks found in the untreated mice (39.8 in average) to determine the inhibition ratio. A ratio of more than 50% was evaluated as an effective ratio. The results are shown in Table 8. In this table, the numbers of the pocks found in the untreated group were 28 in average.

TABLE 8

| | Inhibition ratio in average (%) | | | |
|---|---|---|---|---|
| | | Sample | | |
| Concentration | (mg/kg) | A | B | C |
| Iv. | 40 | 96 | 99 | 98 |
| | 4 | 95 | 100 | 99 |
| | 0.4 | 63 | 97 | 92 |
| | 0.04 | 23 | 65 | 60 |
| Ip. | 40 | 80 | 97 | 95 |
| | 4 | 22 | 55 | 50 |
| | 0.4 | <10 | 20 | 16 |
| | 0.04 | <10 | <10 | <10 |
| Oral | 4000 | 42 | 70 | 68 |
| | 400 | 15 | 25 | 23 |

(2) Mouse (Herpes Simplex virus)

Herpes Simplex virus was used instead of Vaccinia virus. In a similar manner to that described in B(1), the samples were injected (iv. or ip.) or orally administered with the sample and the virus was infected by injection (ip.). After this, the test animals were observed for 30 days to investigate the survival days which were then compared with the corresponding days of the untreated group. A significant effect on the elongation of the life spun was observed.

(3) Rabbit (Vaccinia virus)

(a) Rabbits (each group consisting of 5 rabbits) were used as test animals, and a physiological sodium chloride solution (each 0.1 ml) containing sample A was injected into the skin at the back of each animal. After 24 hours, a physiological solution of sodium chloride (each 0.1 ml) containing 10 $ID_{50}$ of the virus [1 $ID_{50}$ denotes an amount of the virus used when 50% of the pocks formed under the skin of the test animal are more than 6×6 mm in size] was injected into the same place, and the numbers of the formed pocks were counted on the 7th day from the infection. The sample of the active substance used was stepwise diluted (×10) within a range of from 0.02 to 200 μg. It was found that a dose of more than 2 μg resulted in a 100% inhibition ratio.

(b) Each rabbit of the test group (each group consisting of 5 rabbits) was orally administered with sample A (each 100 mg/day) 5 times (on the first, 3rd, 4th, 6th and 8th days). On the 5th day, 10 $ID_{50}$ and 100 $ID_{50}$ of the virus were separately injected into the skin at the back of each rabbit. On the 12th day, it was observed that no pock was formed on the rabbits infected with 10 $ID_{50}$ and a minute quantity of the pocks was formed on the rabbits infected with 100 $ID_{50}$. However, the latter pocks disappeared completely in about 2 weeks.

(C) Anti tumour effect (mouse)

(1) Ehrlich ascites tumour

Mice (each group consisting of 15 mice) were used as test animals. A sterlized water (each 0.2 ml) containing Ehrlich ascites tumour cells (2.5×10⁶ cells/0.2 ml) was transplanted into each mouse by injection (ip.). 24 hours after this, a given amount of sample B in sterilized water (each 0.2 ml) was given to each animal. The administration was effected once daily for 14 days at a daily dose of 0.2, 1.0 or 5 mg/kg (ip) or 40, 200, or 1000 mg/kg (orally). By administration of 1 or 5 mg/kg/day (ip), the median survival days were 42 days and moreover ½ of the test mice were not only still alive 50 days after the transplantation but also completely cured. On the other hand, all mice of the untreated group were not alive on or after 29 days from the transplantation.

A similar effect was found when the sample was injected (ip) 5 times (1.0 mg/kg/day) at an interval of 3 days. Also, a similar effect was found by oral administration of 100 mg/kg/day.

(2) S-180 Sarcoma Solid tumour

Mice (each group consisting of 15 mice) were used as test animals. A sterilized water (each 0.2 ml; containing 1×10⁵ tumour cells) was transplanted into each mouse under the skin at the armpit. Sample B was given to the mice in a similar manner to that described above. By administration of 5 mg/kg/day (ip)/mouse, the median survival days were 42 days and on or before 40 days after the transplantation, the tumours of 4 mice were reduced to about ½ in size and 2 mice were completely cured. By administration of 400 or 1000 mg/kg/day orally, the results obtained were similar to the results obtained by injection (ip). All mice of the control group deceased on or before 35th after transplantation.

(D) Combined use of IF and IF inducer (priming effect)

(1) A suspension containing lymphoid cells of rabbits ($10^7$ cells/ml) was prepared by the method of hereinafter described Experiment 1 and was added with rabbit IF (30 unit/ml). The mixture was treated at 37° C. for 6 hours and was then centrifuged to remove the IF. Then an Eagle MEM medium (1 ml) and sample B were added to the cells and its activity was determined with simultaneous change of the amount of sample B from $10^{-3}$ to $10^{-7}$ mg/ml. It was found that the activity of the induced IF raised to about 3–10 folds and also the response of the cells was significantly improved.

(2) By the method of hereinbefore described (D,1), a suspension of human spleen cells ($10^7$ cells/ml) was prepared and and treated with human IF (100 unit/ml). The activity of the IF raised to about 3–6 folds and also the response of the cells to the IF was improved siginificantly.

(3) Each of rabbits (each group consisting of 5 rabbits) was intravenously administered with rabbit IF (each $10^6$ units) and after 6 hours sample B was administered in a similar manner to that described in (A)-(II)(1). It has been found that the IF activity in the serum was raised to about 3 to 10 folds and also the effective period of time of the IF induction was extended.

(4) Each of rabbits (each group consisting of 5 rabbits) was intravenously administered with rabbit IF (each $10^6$ units). On the next day, a test on the protection of viral infection was begun in a similar manner to that described in (B)(3)(b). No pock was formed at the sites infected with 10 $ID_{50}$ of the virus. Minor pocks were formed at ⅓ of the locations infected with 100 $ID_{50}$ of the virus, which were however disappeared completely in 2 weeks after the infection.

(E) Toxicity (1) Acute toxicity

A physiological sodium chloride solution containing sample B was administered to each of the mice (male and female; each group consisting of 20 mice) and rats (male and female; weight about 95 g; SPF-SD strain; 6 weeks old; each group consisting of 20 rats) to obtain the $LD_{50}$ values shown in the following table, from which no significant difference was observed between male and female.

TABLE 10

| | Acute toxicity ($LD_{50}$) | | | |
| | Concentration of sample (g/kg) | | | |
| Animal | Subcutaneous | Ip | Iv | Oral |
|---|---|---|---|---|
| Mouse | >2 | >1.5 | 1.2 | >5 |
| Rat | >1 | >1.5 | 1.25 | >5 |

(2) Subacute toxicity

Rats (weight about 95 g; SPF-SD strain; 6 weeks old; each group consisting of 20 rats) were used as test animals. Sample A was divided into fractions (0.35, 0.7, 1.4 and 2.8 g/kg), each of which was added to each sterilized water (from 0.25 to 0.5 ml), and a given amount of the sample was daily administered to the test animals compulsively by using a canule. The administration was continued for 3 months. In comparison with the untreated animals, the healthy conditions of the test animals were improved throughout the test period and their body weights increased at a remarkably high ratio. All animals were dissected after the end of 3 months and investigated pathologically. However, it was difficult to determine the subacute toxicity reasonably because no significant change was observed pathologically.

(b) Five healthy men (adults) were administered orally with sample A (200 mg/day) and the administration was continued for 10 days. As a result, no significant side effect was observed.

For the purpose of administering the active substance of this invention to humans and animals with good results, there is provided a pharmaceutical composition, which comprises as active ingredient an effective amount of the active substance of this invention as hereinbefore defined, in association with a pharmaceutical carrier or excipient.

The composition may be any and all forms adapted to oral, rectal, perenteral, percutaneous, intramucous administration and the like. Thus, for example, the composition may be solid or liquid for oral administeration and may take the forms of powders, syrups, capsules, granules, emulsions, suspensions, drops and the like. Such composition comprises carrier or excipient conventionally used in the pharmaceutical art. Thus, for example, suitable tabletting excipients include lactose, potato and soluble starch and magnesium stearate, and for parenteral administration, the carrier may be a steril water, physiological solution of sodium chloride, armond oil and the like, which may be put in an ampule or may be added to the active substance before use.

The composition may, if desired, further comprises, for example, bonding agents, stabilizing agents, emulsifiers, suspending agents, dispersing agents, lublicants, antiseptic agents, fillers and the like conventionally used in the pharmaceutical art. Such composition comprises carrier or excipient conventionally used in the pharmaceutical art. Thus, for example, suitable tabletting excipients include lactose, potato and soluble starches and magnesium stearate and for parenteral administration, the carrier may be a sterile water, physiological solution of sodium chloride, armond oil and the like, which may be put in an ampule or may be added to the active substance before use.

The composition may, if desired, further comprise, for example, bonding agents, stabilizing agents, emulsifiers, suspending agents, dispersing agents, lublicants, antiseptic agents, fillers and the like conventionally used in the pharmaceutical art.

For practical purpose, the composition may be formulated, for example, as buccals, troches, eye drops, suppositories and the like for intramucous administration, solutions, oils, suspensions and the like for injection agents, inhalants, sprays and the like for inhalational administration and ointments, plasters, liniments, bathes, sprays and the like for external administration.

Advantageously, the composition may be formulated as dosage units, each unit being adapted to supply a fixed dose of active ingredient. Suitable dosage unit forms are, for example, tablets, coated tablets, ampules, capsules, suppositories and the like.

The amount of the active ingredient preferably contained in such dosage unit forms may, for example, be within a range of from about 4 to about 10 for oral administration, about 2-3 for subcutaneous administration, about 1.5-3 for intramuscular administration, about 2-4 for baccals and troches and about 5-10 for suppositories, calculated on the basis of the preferred amount for intravenous injection. Examples of unit dosage forms are as follows.

| (1) | Parenteral injection: | |
|---|---|---|
| | Physiological solution of NaCl | 1.0 ml |
| | Sample B | 0.01 g |
| | packed and sealed in a 2 ml ampule under sterilized conditions. | |
| (2) | Troch: | |
| | White sugar | 1 g |
| | Sample B | 0.05 g |
| | Starch | 0.05 g |
| (3) | Suppository: | |
| | Polyethylene glycol 400 | 0.8 g |
| | Liquid polyethylene glycol 1500 | 0.2 g |
| | Sample A | 0.2 g |
| (4) | Syrup: | |
| | CMC-Na | 0.2 g |
| | Simple syrup | 20 g |
| | Ethylparaffin | 0.04 g |
| | Sample B | 0.1 g |
| (5) | Ointment: | |
| | Purified lanolin | 5 g |
| | Yellow wax | 5 g |
| | White vaselin | 87 g |
| | Sample B | 3 g |
| (6) | Liniment: | |
| | Potassium hydroxide | 0.3 g |
| | Glycerin | 20 ml |
| | Ethanol | 25 ml |
| | Sample B | 2.5 g |
| | Make-up water | to 100 ml |

DRAWINGS

FIGS. 1 and 2 show respectively the ultraviolet and infrared absorption spectra of the active substance of this invention.

PREFERRED EMBODIMENTS

The following examples illustrate the preparation of the active substance of the present invention.

EXAMPLE 1

Dried flowers (2 kg) of *Carthamus tinctorius* Linne were washed with water and allowed to stand in water (40 liter) at room temperature for 3 days to effect exraction, followed by centrifugation (6000 r.p.m.) for 20 minutes to remove the residue which was then washed twice with water (each 10 l). The washing liquid was combined with the supernatant, and the combined solutions were fractionated by using an ultrafilter (Model UD-6, commercial product of Bio Engineering K.K., Tokyo) with a UK 200 membrane (commercial product of Toyo Roshi K.K., Tokyo) for retaining substances having a molecular weight of more than 200,000 at a pressure of 3 kg/cm$^2$ to give a residue which was then freeze-dried to obtain a brown powder (89.46 g). This powder (2 g) was then dissolved in water (5 ml) and transferred to a column (4.5×70 cm) packed with Sephadex G-200 (an agent for gel filtration, commercial product of Pharmacia Fine Chemicals AB., Sweden). The elution was effected with water (600 ml) and the effluent was divided into fractions (each 3 ml). Fractions Nos. 25–55 were collected and combined, and the combined fractions were freeze-dried to obtain whitish powders (155.04 mg).

For further purification, this powder (100 mg) was dissolved in a 0.01M tris-HCl buffer solution (5 ml; pH 7.0; I=0.01) and transferred to a column (2.5×70 cm) packed with DEAE-Sephadex A-50 (an ion exchanger, commercial product of Pharmacia Fine Chemicals AB., Sweden). The elution was effected with a 0.1M tris-HCl buffer solution (300 ml; pH 9.0; containing 0.5M NaCl). The effluent was divided into fractions (each 3 ml) and Fraction Nos. 16 to 27 were collected and combined, and the combined fractions were desalted by ultrafiltration using UK-10 membrane (commercial product of Toyo Roshi K.K., Tokyo) for fractionating substances having a molecular weight of 10,000, followed by freeze-drying to give an amorphous whitish powder (72.3 mg), of which physico-chemical and biological characteristics are as hereinbefore described. When compared with the first whitish powder, the second whitish powder exhibits a substantially the same IF inducing activity and contains smaller amounts of impurities, although its high purity was confirmed by ultracentrifugation and electrophoresis.

For comparison purpose, the IF inducing activities of the substances obtained by respective steps in this example were determined in a similar manner to that hereinafter described in Experiment 1 (in vitro method) to give the results shown in the following table.

TABLE 7

| | IF activity | | | |
|---|---|---|---|---|
| | Concentration of sample | | | |
| After the step of | 10 | 1.0 | 0.1 | (μg/ml) |
| Extraction | >100 | <10 | <10 | |
| Ultrafiltration | >100 | 15 | <10 | |
| Gel filtration | >100 | >100 | 96 | |
| Ion exchange treatment | >100 | >100 | >100 | |

EXAMPLE 2

Dried flowers (1 kg) of *Carthamus lanatus* Linne were washed with water, added with water (20 l) and allowed to stand at room temperature for 2 hours. After this, the extraction was effected by heating the mixture at 100° C. for 2 hours. The mixture was then treated in a similar manner to that described in Example 1 to give a purified product (70.3 mg), of which physico-chemical and biological characteristics were substantially the same as those of the purified product obtained by Example 1.

EXPERIMENT 1

Determination of IF induced by IF inducer and IF assay: [Reference: Y. Kojima's report in Kitasato Arch. Med., 43:35 (1970)]

(a) IF induction in vitro:

A rabbit (weight about 1 kg; New Zealand White; SPF) was sacrificed by cardic puncture and its spleen, bone marrow and lymph node cells were collected and combined together, from which a cell suspension containing the mixed cells ($10^7$ cells/ml) was prepared using an Eagle MEM medium (commercial product of Nissui Seiyaku K.K., Tokyo) containing a 10% calf serum. This suspension was divided into fractions (each 1 ml), and 4 fractions were respectively added with 10, 1.0, 0.1 and 0.01 μg/ml of an active substance prepared by the method of Example 1, which was incubated at 25° C.

for 24 hours, followed by centrifugation to obtain each supernatant which was then used to determine the activity of the IF induced.

(b) IF induction in vivo:

An aqueous solution (2 ml) of the active substance prepared by the method of Example 1 (500 μg/ml) was injected into the auticular vein of a rabbit (weight about 1 kg; New Zealand White; SPF). 1, 2 4 and 6 hours after this, a 2 ml sample of blood was removed from the rabbit on each occasion and used to prepare the serum used to determine the IF activity.

(c) Determination of IF activity:

In both (a) and (b), the activity of the IF induced was determined in reliance with the reduction ratio of plaques in the following manner.

A monolayer culture of the lined cells RK-13 of rabbit was put in a dish and added with a predetermined amount of the solution obtained by the method (a) or (b) (suitably diluted). The culture was incubated at 37° C. overnight. After this, the culture was added with Vesicular stomatitis virus used as the challenge virus and further cultured at 37° C. overnight. The IF activity is indicated by the reduction ratio of plaques and the unit of the IF activity is expressed by the reciprocal number of the highest dilution of the sample required for reducing the numbers of plaques to 50%.

EXPERIMENT 2

Definition of IF inducer:

The active substance of this invention represents an IF inducer because the samples prepared by the methods (a) and (b) are capable of inhibiting the growth of Vesicular stomatitis virus and Vaccinia virus in the lined RK-13 cells of rabbits of the same animal species, but do not inhibit the growth of Vesicular stomatitis virus in L cells of mice i.e. of a different animal species, and moreover, their IF activities are inactivated by treating with 0.08% trypsin at 37° C. for 2 hours. It has also been found that the IF induced by the active substance of this invention is stable when dialized against a pH 2 buffer solution at 5° C. for 2 days, unstable on heating at 60° C. for 2 hours, gives no precipitate by centrifugation at 100,000×g for 2 hours and is non-toxic against the cells at the minimum virus-inhibitory level. The IF induced by the active substance of this invention may be classified into Type-I IF and consists of a complex of α- and β-types. Also it has been observed that IF is induced when the active substance of this invention is used, for example, for treating the cells of bone marrow, lymph node, spleen and the like in vitro or injected into the body of animals, but no IF is induced when applied to treat the primary or continuous cell cultures which are known to induce IF by viral infection or treating with poly I:poly C.

EXPERIMENT 3

In Example 1, the electrophoresis was effected at 4° C. in conventional manner using a commercially available device (Model AE-2, product of Toyo Kagaku Sangyo K.K., Tokyo), a polyacrylamide gel plate (thickness 3 mm) and a 0.3M boric acid buffer (pH 8.4). The resultant single band indicated that the rest sample had a high putity.

EXPERIMENT 4

Determination of the specific IF activity in vitro:

(A) In a similar manner to that described in Example 1, dried flowers (2 kg) of *Carthamus tinctorius* L. were extracted with water (40 l) to give an extracted solution (dry weight 562.037 g) which was subjected to ultrafiltration using a membrane (UK-200) capable of fractionating substances having a molecular weight of more than 200,000 to give a residue and filtrate. The residue was freeze-dried to obtain a crude powder (dry weight 89.46 g) referred to as Fraction No. I. The filtrate was similarly treated by using a membrane (UK-10, commercial product of Toyo Roshi K.K., Tokyo) capable of fractionating substances having a molecular weight of more than 10,000 to give a residue and filtrate, both of which were respectively freeze-dried to give solid substances referred to as Fractions II (dry weight 22.28 g) and III (dry weight 450.28 g). All fractions were respectively used to determine IF activities induced in vitro by the method of Experiment 1. It was found that Fraction I was active and no or little activity was present in Fractions II and III. After this, Fraction I (2 g) was dissolved in water (5 ml) and applied to a column (4.5×70 cm) packed with Sephadex G-200 (commercial product of Pharmacia Fine Chemicals AB, Sweden) to effect gel filtration with water (600 ml) and the effluent was divided into fractions (each 3 ml). 0.5 Ml of each fraction was used to develop the colour by the phenol/sulfuric acid method and its absorption at 485 mμ was determined by using a spetrophotometer (Model 40-100, commercial product of Hitachi Limited, Tokyo). In reliance with the peaks observed, all fractions were classified and combined to give 5 groups (I-1 to I-5). Each group was freeze-dried and used to determine the IF activity induced in vitro by the method of Experiment 1. The results are shown in the following table.

TABLE A

| Fraction (molecular weight) | Yield (%)* | Recovery ratio (%) | IF activity in vitro at a concentration of | | | |
|---|---|---|---|---|---|---|
| | | | 10 | 1.0 | 0.1 | μg/ml |
| After ultrafiltration | | | | | | |
| All extracts | 28.102 | | >100 | <10 | <10 | |
| I (>200,000) | 4.473 | 15.92 | >100 | 95 | <10 | |
| II (200,000–10,000) | 1.114 | 3.96 | 43 | <10 | <10 | |
| III (<10,000) | 22.514 | 80.12 | <10 | <10 | <10 | |
| After gel filtration | | | | | | |
| I-1** | 0.347 | 8.86 | >100 | >100 | 96 | |
| I-2 | 0.220 | 5.61 | 60 | <10 | <10 | |
| I-3 | 0.346 | 8.83 | <10 | <10 | <10 | |
| I-4 | 2.678 | 68.35 | <10 | <10 | <10 | |
| I-5 | 0.327 | 8.35 | <10 | <10 | <10 | |

*100% = dry weight of starting material
**Fraction Nos. 27–50 in Example 1

(B) Dried flowers of *Carthamus tinctorius* L. (50 g) were washed with water, added with water (1000 ml), allowed to stand at room temperature for 2 hours, heated to 100° C. for 30 minutes, cooled to room temperature and centrifuged for 30 minutes (8000 r.p.m.) to separate the filtrate from the residue. The residue was washed twice with water (each 200 ml) and the washing liquid was combined with the filtrate. The combined solution (dry weight of solid content: 14.509 g) was treated in a similar manner to that described in Example 1 by using a membrane capable of retaining substances having a molecular weight of more than 200,000 (UK-200) to give a filtrate and residue. The residue was freeze-dried to obtain a solid (dry weight 1.774 g) which was then subjected to gel filtration in a similar manner to that described in Example 1 to give a solid referred to as Fraction No. 1. The filtrate was treated similarly by using a membrane for fractionating substances having a molecular weight of more than 10,000 (UK-10, commercial product of Toyo Roshi K.K., Tokyo) to give a residue and filtrate, both of which were freeze-dried to obtain solid substances (dry weight 0.63 g, Fraction No. 2; and 11.577 g, Fraction No. 3) respectively. All the fractions were used to determine the IF activities induced in vitro by the method of Experiment 1 to give the results shown in Table B, from which it is apparent that the active substance is prevalent in Fraction No. 1.

TABLE B

| Fraction (molecular weight) | Yield (%)* | Recovery ratio (%) | IF activity in vitro at a concentration of | | |
|---|---|---|---|---|---|
| | | | 10 | 1.0 | 0.1 µg/ml |
| All extracts | 29.018 | | >100 | <10 | <10 |
| I (>200,000) | 3.548 | 12.69 | >100 | 97 | <10 |
| II (200,000–10,000) | 1.260 | 4.50 | 50 | <10 | <10 |
| III (<10,000) | 23.154 | 82.81 | <10 | <10 | <10 |

*100% = dry weight of starting material (C) From (A) and (B), it is apparent that the IF inducing activity is most prevalent in the fraction having a molecular weight of more than 200,000 and that impurities contained in the extracted solution is almost completely removed by ultrafiltration and gel filtration. The amounts of impurities were further reduced by the following ion exchange treatment as described in Example 1 and an increase of about 10% of the specific activity was observed.

We claim:

1. A process for producing a water-soluble interferon inducer from a plant tissue, comprising extracting said interferon inducer with water from the tissue of a plant belonging to the genus Carthamus containing said interferon inducer at a temperature of from ambient to the boiling point of the extraction mixture for a period of up to 5 days sufficient to extract the major portion of said interferon inducer present in said tissue, forming a supernatant from the extracted solution, fractionating the supernatant to yield fractions containing the major portion of said interferon inducer present in the supernatant, and recovering said interferon inducer therefrom.

2. The process of claim 1 wherein the plant is selected from *Carthamus tictorius* Linne; *Carthamus lanatus* Linne; *Carthamus arborescens* Linne; *Carthamus baeticus* Nyman and variants thereof.

3. The process of claim 1, wherein the extracting water has an alkaline pH.

4. The process of claim 5, wherein the pH is 7–10.

5. The process of claim 1, wherein the supernatant is fractionated by ultrafiltration.

6. The process of claim 5, wherein the ultrafiltration is effected by using an ultrafitration membrane for retaining substances having a molecular weight of more than 100,000.

7. The process of claim 1, wherein the fractionation is effected by adding to the supernatant one member selected from hydrophilic organic solvents incapable of dissolving the said interferon inducer and ammonium salts so as to form a precipitate containing a major portion of the said interferon inducer.

8. The process of claim 7, wherein the organic solvent is selected from methanol, ethanol, propanol, butanol, acetone and mixture thereof at a concentration of 40–70 w/v %.

9. The process of claim 7, wherein the ammonium salt is selected from ammonium chloride, ammonium sulfate and cetylmethylammonium bromide at a concentration of 20–50 w/v %.

10. The process the process of claim 1 wherein said interferon inducer has a molecular weight of about 100,000 to about 3,000,000.

11. An amorphous whitish powder effective as an interferon inducer made by the process of claim 1.

12. The interferon inducer of claim 11 having a molecular weight of about 200,000 to about 3,000,000.

13. A pharmaceutical composition comprising as an active ingredient an interferon inducer made by the process of claim 1 in association with a pharmaceutical carrier or excipient.

14. The pharmaceutical composition of claim 13 wherein said interferon inducer has a molecular weight of about 200,000 to about 3,000,000.

* * * * *